United States Patent [19]

Eisenberg

[11] Patent Number: 4,559,942

[45] Date of Patent: Dec. 24, 1985

[54] METHOD UTILIZING A LASER FOR EYE SURGERY

[76] Inventor: William Eisenberg, 16 Park Ave., New York, N.Y. 10016

[21] Appl. No.: 584,923

[22] Filed: Feb. 29, 1984

[51] Int. Cl.⁴ .......................................... A61B 17/36
[52] U.S. Cl. ................................... 128/303; 128/395
[58] Field of Search ........ 128/303.1, 303.17, 395–398, 128/362

[56] References Cited

U.S. PATENT DOCUMENTS

| | | | |
|---|---|---|---|
| 2,247,258 | 6/1941 | Shepard | 128/397 |
| 3,084,694 | 4/1963 | Kavanagh et al. | 128/303.1 |
| 3,471,215 | 10/1969 | Snitzer | 128/398 |
| 3,494,354 | 2/1970 | Yokata et al. | 128/398 |
| 3,804,095 | 4/1974 | Bredemeier | 128/303.1 |
| 3,821,510 | 6/1974 | Muncheryan | 128/303.1 |
| 3,843,865 | 10/1974 | Nath | 128/395 |
| 3,865,113 | 2/1975 | Sharon et al. | 128/303.1 |
| 3,913,582 | 10/1975 | Sharon | 128/303.1 |
| 3,982,541 | 9/1976 | L'Esperance | 128/395 |
| 4,069,823 | 1/1978 | Isakov et al. | 128/303.1 |
| 4,120,293 | 10/1978 | Muckerheide | 128/395 |
| 4,211,229 | 7/1980 | Wurster | 128/395 |
| 4,249,533 | 2/1981 | Komiya | 128/303.1 |
| 4,270,845 | 6/1981 | Takizawa et al. | 128/303.1 |

Primary Examiner—Kyle L. Howell
Assistant Examiner—Ruth S. Smith
Attorney, Agent, or Firm—Browdy and Neimark

[57] ABSTRACT

Surgical apparatus including laser, probe apparatus defining a radiation inlet and a radiation outlet, the radiation inlet being coupled in radiation receiving relationship to the laser, and apparatus for injecting a precisely controllable volume of air adjacent the radiation outlet.

4 Claims, 15 Drawing Figures

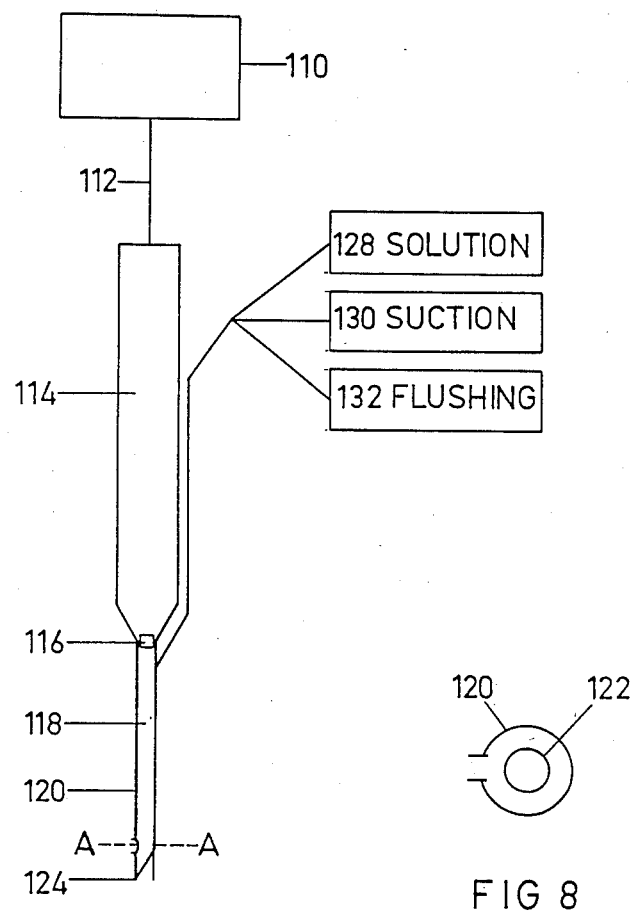
FIG 6
FIG 8
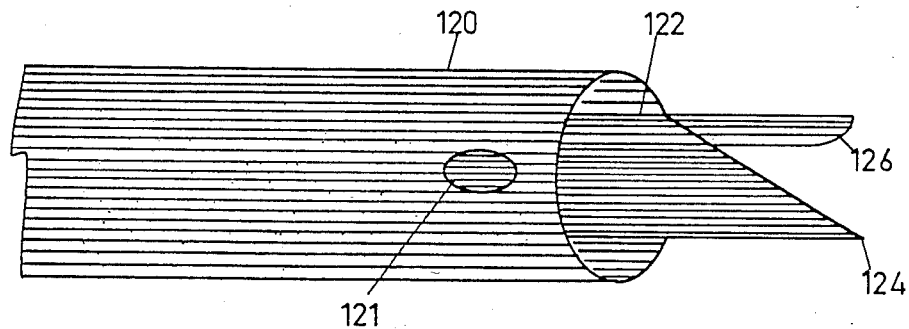
FIG 7

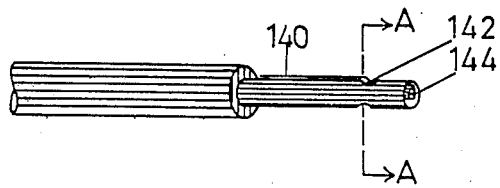
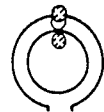
FIG 9A          FIG 9B
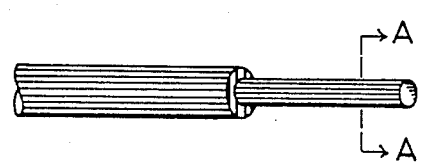
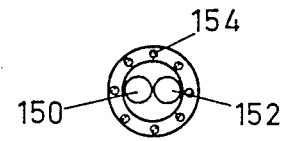
FIG 10A         FIG 10B
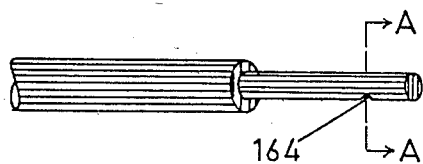
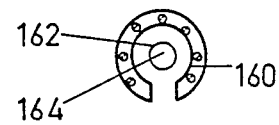
FIG 11A         FIG 11B

METHOD UTILIZING A LASER FOR EYE SURGERY

FIELD OF THE INVENTION

The present invention relates to a surgical method in general and, in particular, to utilizing a laser apparatus for ophthalmic and other delicate surgery.

BACKGROUND OF THE INVENTION

Several devices are known and in use today for performing surgery in small or difficultly accessible parts of the body, such as within the eye. In particular, various operations for the treatment of cataracts or glaucoma or vitrealretinal disorders require specialized apparatus to permit entry into the small volume of the eye and the removal therefrom of the pathologic tissue.

Conventional methods of ophthalmic surgery include the traditional technique of manual removal of the lens, the use of intraocular scissors to cut membranes, intracapsular cataract extraction with a cryoprobe, extracapsular cataract extraction, and phaco-emulsification.

Phaco-emulsification, or the so-called Kelman technique, involves the production of ultrasonic vibration of a hand-held probe, generally a titanium needle, contacting the lens or cataract. Suction means is provided through the needle for the removal of the cataract debris, and fluid flushing means is provided adjacent the needle for the inflow of artificial aqueous into the eye to prevent collapse of the eye and to cool the vibrating needle and the area in contact with it.

This method suffers from a number of disadvantages. First, the nucleus may fragment, causing corneal damage, or the nucleus may be too hard to emulsify. Second, rupture of the posterior capsule can occur easily with ultrasonic devices. Third, a great deal of manual dexterity and skill on the part of the surgeon is required to properly perform the operation. Fourth, a large amount of irrigation, or fluid exchange, is required in the anterior segment, greatly increasing the chance of corneal damage. And fifth, the likelihood of iris injury is high.

Intraocular photo-coagulation can be accomplished by means of an ophthalmic argon laser system, such as the Britt Model 152, manufactured and marketed by Britt Corporation, Los Angeles, Calif., U.S.A. This system utilizes an argon laser to deliver energy in the form of very high power via a probe including, for example, a fiber optic or quartz fiber needle to irradiate the target area of the eye.

Yet another photo-coagulation method is the Xenon Arc method which also utilizes light energy to perform ophthalmic surgery via a fiber optic delivery system. In conventional Xenon Arc systems, a great deal of light is reflected into the surgeon's eyes.

The argon laser and Xenon Arc methods suffer from additional disadvantages. Both require the presence of large lasers in the operating room which is both inconvenient and very costly, thus limiting the availability of these techniques to wealthy hospital facilities. Furthermore, while they deliver satisfactory coagulation burns to the retina, both require a pigmented tissue to be present for the absorption of their energy, and that the retinal tissue be flat against the pigmented epithelium. Finally, one cannot utilize these devices to perform photo-transections, i.e., to make incisions, or photo-cauterizations, i.e., to seal bleeding vessels, procedures which it is often desired to perform during ophthalmic surgery.

Additionally, at present, there are a number of techniques utilizing carbon dioxide lasers to perform ophthalmic surgery. These methods are, for the most part, experimental and require the presence in the operating room of a large carbon dioxide laser coupled by a delivery system including an articulating arm to a probe. One such laser system on the market today is the Sharplan laser manufactured in Israel. This system has the advantage that the carbon dioxide laser is operative on any tissue and does not require the presence of pigmented tissue. However, these probes require physical contact with the target site for coagulation, which often results in mechanical disruption of the tissue. Furthermore, the articulating arm delivery system makes surgery somewhat difficult.

It will be appreciated that all of these photo-coagulation techniques are thermal techniques. Since they require physical contact of the probe with the tissue to be operated upon, a great deal of energy is required to perform the desired operation, due to the heat sink effect of the probe itself. For example, present day carbon dioxide lasers operate at 4 watts.

SUMMARY OF THE INVENTION

It is therefore an object of the present invention to provide a method utilizing a laser apparatus for ophthalmic and other delicate surgery, particularly retinal or vitreous surgery, which requires relatively little energy, which is compact and easily manipulable and which does not suffer from the disadvantages of the prior art devices.

There is thus provided in accordance with the present invention a method utilizing a surgical apparatus including a carbon dioxide laser, a probe apparatus defining a radiation inlet and a radiation outlet, the radiation inlet being coupled in radiation receiving relationship to the laser, and an apparatus for injecting a precisely controllable volume of air adjacent the radiation outlet.

According to a preferred embodiment, the probe apparatus includes a waveguide and the radiation inlet includes an optical window. The radiation outlet may be an aperture at the tip of the waveguide, or it may include a radially offset aperture and a mirror for reflecting the laser radiation therethrough.

Further in accordance with a preferred embodiment, the apparatus for injecting includes a peristaltic pump.

Still further in accordance with a preferred embodiment, the surgical apparatus also includes an angled lifting member.

There is provided in accordance with the present invention a surgical method including the steps of coupling a carbon dioxide laser to surgical probe apparatus defining a radiation inlet and a radiation outlet, moving the probe apparatus adjacent the target tissue, injecting a precisely controllable volume of air between the radiation outlet and the target tissue, and providing carbon dioxide laser radiation from the laser through the probe apparatus to the target tissue while maintaining the volume of air between the probe apparatus and the target tissue.

There is additionally provided in accordance with the invention a method of cataract emulsification comprising the steps of irradiating the cataract with a pulse of radiation from a Neodymium YAG, $CO_2$ or Erbium YLF laser, removing the cataract debris created thereby, and repeating the steps of irradiating and removing until the cataract is removed.

BRIEF DESCRIPTION OF THE DRAWINGS

The apparatus and method of the present invention will be further understood and appreciated from the following detailed description taken in conjunction with the drawings in which:

FIG. 6 is a schematic illustration of apparatus for emulsification of cataracts constructed and operative in accordance with an embodiment of the present invention;

FIG. 7 is a detail illustration of the probe of the apparatus of FIG. 6;

FIG. 8 is a sectional illustration taken through line A—A on FIG. 6;

FIG. 9A is a schematic illustration of alternate probe apparatus operative in the surgical apparatus of the present invention;

FIG. 9B is a sectional illustration taken through line A—A on FIG. 9A;

FIG. 10A is a schematic illustration of alternate probe apparatus operative in the surgical apparatus of the present invention;

FIG. 10B is a sectional illustration taken through line A—A on FIG. 10A;

FIG. 11A is a schematic illustration of alternate probe apparatus operative in the surgical apparatus of the present invention;

FIG. 11B is a sectional illustration taken through line A—A on FIG. 11A.

DETAILED DESCRIPTION OF THE INVENTION

Figure 1:
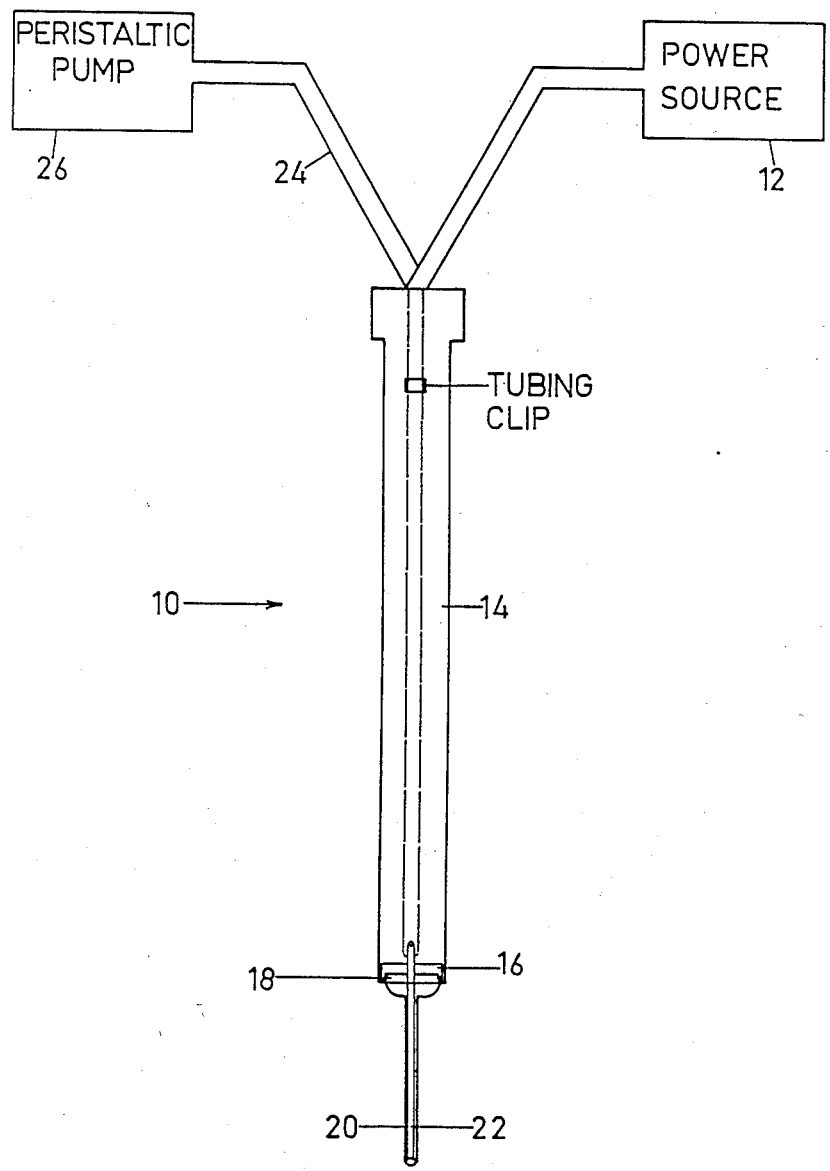
FIG. 1 is a schematic illustration of laser apparatus constructed and operative in accordance with an embodiment of the present invention.

Referring now to FIG. 1 there is shown surgical apparatus constructed and operative in accordance with an embodiment of the present invention and including a waveguide laser, generally designated 10, coupled to a power source 12. Power source 12 may be any conventional power source suitable for powering a carbon dioxide laser operating at about 2 watts.

Laser 10 comprises a carbon dioxide waveguide laser. Due to the construction of the remainder of the surgical apparatus, which will be explained hereinbelow, the laser 10 may be a relatively small carbon dioxide laser, operating between 1 and 2 watts, and will still yield photo-coagulation results comparable to conventional devices.

Laser 10 comprises a waveguide or laser delivery handpiece 14, which is preferably pencil size, to permit ease of manipulation by the surgeon. Waveguide 14 may be of any conventional construction. Mounted at the distal end thereof is an optical window 16 through which the laser radiation passes when the apparatus is in use.

Removably mounted onto waveguide 14 as by threaded attachment portion 18 is an intraocular probe 20 adapted for insertion into the eye or other surgical location and adapted to transmit the laser radiation to the target tissue. Probe 20 may comprise any probe of suitable length and diameter for the particular operation being performed. According to one preferred embodiment of the invention, the waveguide, or handpiece, is 4 inches long and ½ inch in diameter, having a diamond optical window, which can be used for the transmission and, if desired, focusing of the radiant energy, and the probe comprises a 2.5 cm long 18 to 20 gauge needle. The diamond window is capable of transmitting and focusing 100% of the $CO_2$ radiant energy, without being damaged by the irradiation.

Probe 20 also includes air injection means 22 coupled to a source of pressurized air 26 as via air conduits 24. Air injection means 22 provides a precisely controllable volume of air adjacent the tip of probe 20. According to a preferred embodiment, the source of pressurized air 26 is a peristaltic pump and the air injection means comprises a hollow conduit coupled to or about the probe needle.

The operation of the surgical apparatus of this embodiment is as follows. The surgeon holds handpiece 14 and moves the tip of intraocular probe 20 adjacent the target tissue. With the probe in a wet field, air source 26 is actuated to provide a small volume of air to air injection conduit 22, thereby generating a small air bubble between the probe 20 and the target tissue.

It is a particular feature of the present invention that an air/tissue interface is generated and maintained throughout the laser irradiation of the body tissue. This has a number of beneficial results. First, there is no direct contact between the probe and the target tissue which acts to avoid mechanical disruption of the tissues. Second, due to the air cushion between the probe and the target tissue, the carbon dioxide laser radiation passes from the probe to the tissue with little attenuation and with little loss of heat, thus requiring much less energy than required by conventional laser systems for successful photo-coagulation. For example, production of a satisfactory lesion on the retina using the apparatus of the present invention requires only $8 \times 10^{-3}$ joules.

It will be appreciated that the utilization of a carbon dioxide laser has the added advantage of permitting irradiation of any desired tissue without the need for pigmentation. Furthermore, due to the provision of an air cushion or air/tissue interface during surgical procedures, the apparatus of the present invention is operative for photo-cauterization and photo-incision, as well as photo-coagulation. In particular, the apparatus is useful for retinal or vitreous surgery including transvitreal coagulation of retinal tissue, photo-cauterization and photo-incision of retinal tissues.

Figure 2A:
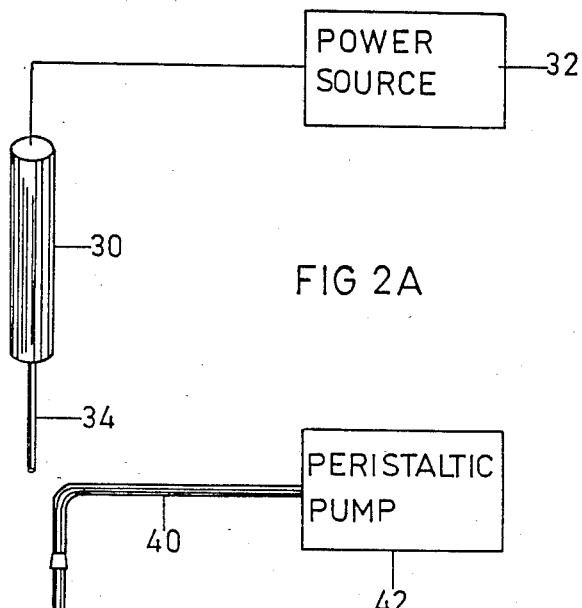
FIGS. 2A and 2B are an exploded view illustration of laser apparatus constructed and operative in accordance with an alternate embodiment of the present invention, FIG. 2A illustrating the laser and probe and FIG. 2B illustrating the air infusion mechanism.
Figure 2B:
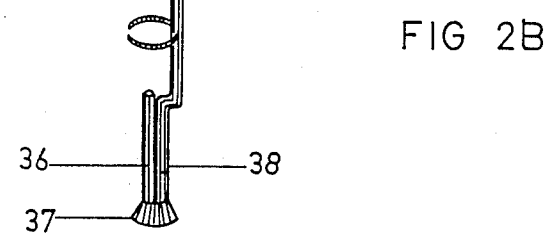

Turning now to FIGS. 2A and 2B there is shown surgical apparatus constructed and operative in accordance with an alternate embodiment of the present invention in an exploded form. Similarly to the embodiment of FIG. 1, the apparatus includes a laser handpiece 30 coupled to a power source 32 and an intraocular probe 34. The handpiece is arranged for seating within a laser support member 36 which defines a flared portion 37 at the base of the probe. Affixed to laser support member 36 is air injection tube 38 coupled via plastic tubing 40 to a source of pressurized air 42, preferably a peristaltic pump. It is a particular feature of this embodiment of the invention that the flared portion 37 of the laser support member permits the air bubble or cushion formed during surgery to spread out under the laser, thereby insuring accurate transmission.

The operation of the apparatus of this embodiment is substantially identical to that of the embodiment of FIG. 1. It will be appreciated that the carbon dioxide laser need not be a waveguide laser, although that is preferred. The laser may be a conventional laser provided with a manipulable handpiece to which is coupled the air injection means.

Furthermore, the laser support and air injection apparatus of FIG. 2B can alternately be employed with a conventional intraocular Argon probe to provide an air/tissue interface during Argon probe surgery. This is advantageous as the detached retinal tissue can be flattened by mechanical means associated with the bubble interface against the pigmented tissue prior to photocoagulation.

Figure 3:
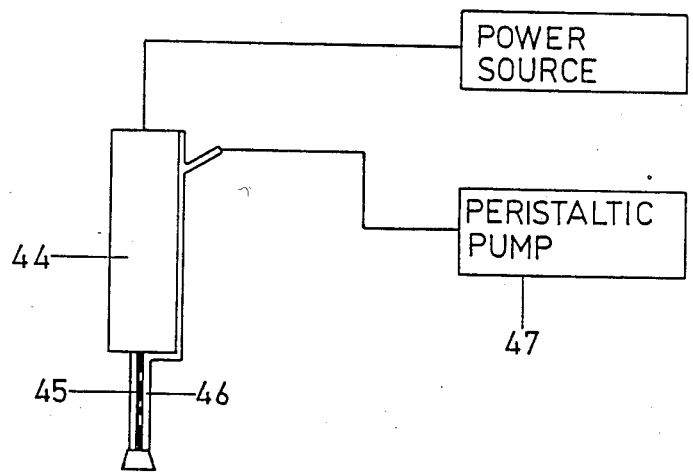
FIG. 3 is a schematic illustration of laser apparatus constructed and operative in accordance with an alternate embodiment of the present invention.

With reference to FIG. 3, there is shown apparatus according to yet another embodiment of the present invention. This embodiment comprises a laser 44, its probe 45 being mounted within a bubble sleeve 46 which serves to conduct pressurized air from a supply of pressurized air 47 for formation of an air bubble or cushion at the tip of the laser probe. In this embodiment, the bubble sleeve slips around the laser probe, as opposed to the embodiment of FIGS. 2A and 2B wherein the laser probe fits into a laser support tube adjacent the air injection tube.

Figure 4:
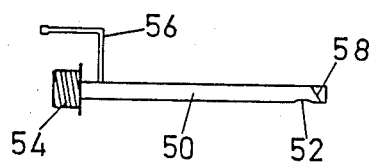
FIG. 4 is a schematic illustration of probe apparatus operative in the surgical apparatus of the present invention.

Referring now to FIG. 4, there is shown a detail view of an alternate embodiment of the intraocular probe operative in the apparatus of the present invention. This probe comprises a hollow elongate tube 50 defining an aperture 52 in one side thereof adjacent the distal tip. The proximal end defines screw threads 54 or other connecting means for coupling the probe to the laser. Adjacent the proximal end is also located an air inlet port 56. Mounted in the distal end of tube 50 is a mirror 58 which is mounted in such a way that laser radiation impinging thereon from the laser (not shown) will be reflected out through aperture 52.

In operation, the aperture 52, which is the active portion of the probe, is placed adjacent the target tissue in a wet field. The injection of air via air inlet port 56 through tube 50 creates an air bubble through aperture 52. When a pulse of laser radiation is provided by the laser, the radiation is reflected by mirror 58 through aperture 52 and the air bubble therein to the target tissue. This embodiment is particularly useful for cataract and glaucoma surgery.

Figure 5:
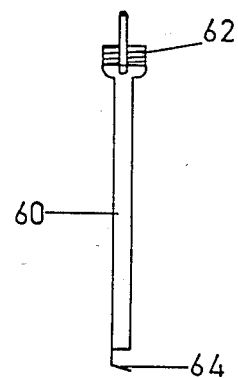
FIG. 5 is a schematic illustration of alternate probe apparatus operative in the surgical apparatus of the present invention.

FIG. 5 illustrates yet another embodiment of the probe of the present invention. It comprises an elongate hollow tube 60 defining coupling means, as screw threads 62, at one end thereof. At the distal end thereof, tube 60 defines a bent tip or angling member 64. Member 64 serves to lift pathologic tissue so as to permit the irradiation of a particular layer of tissue. In operation it is substantially similar to the previous embodiments except that an air bubble is generated on the angling member itself.

Turning now to FIGS. 6, 7 and 8, there is shown surgical apparatus for the emulsification of cataracts constructed and operative in accordance with the present invention. The apparatus includes a Neodymium YAG, CO 2 or Erbium YLF laser 110 coupled as by an optical fiber 112 to a handpiece or waveguide 114 defining an optical window 116. Adjacent optical window 116 and in radiation receiving contact therewith is probe means 118 which comprises outer and inner concentric elongate hollow tubes 120 and 122.

Outer tube 120 defines an aperture 121 which permits the inflow of aqueous fluid into the target area during surgery. Inner tube 122 preferably defines at its distal end a truncated tip 124 formed by cutting tube 122 to form an elliptical cross section. The elliptical tip provides easier insertion into the eye as well as being useful for removing the nuclear cataract material. However, a straight cut tip can also be employed effectively.

According to a preferred embodiment, wherein inner tube 122 defines a truncated tip, a shield 126 may be affixed to tube 120 opposite tip 124. Shield 126 serves to protect the cornea from radiation during the surgical process.

The apparatus further comprises a source of aqueous solution 128 coupled to outer tube 120 and a suction source 130 coupled to inner tube 122 and a reverse flushing mechanism 132 also coupled to inner tube 122. As during conventional cataract emulsification, it is necessary to introduce aqueous solution into the eye to prevent collapse thereof. This is done from aqueous solution source 128 via outer tube 120 during the irradiation of the cataract. At the same time, it is necessary to remove the cataract debris which is created by the emulsification of the cataract. This is done by suction source 130 via inner tube 122. The reverse flushing mechanism 132 serves to clear blockages of inner tube 122.

FIGS. 9A and 9B illustrate an alternative embodiment of the invention, illustrated in FIGS. 6–8 wherein the laser radiation is carried by an optical fiber 140 which extends externally of outer tube 120 and whose distal end is inserted via aperture 142 and 144 into respective outer and inner tubes 120 and 122 adjacent the distal ends thereof.

FIGS. 10A and 10B illustrate a further alternative embodiment of the invention shown in FIGS. 6–8 wherein the probe comprises irrigation and asperation- tubes 150 and 152 surrounded by a fiber optical cable 154 carrying the laser radiation.

The embodiment of FIGS. 11A and 11B differs from that shown in FIGS. 10A and 10B in that here coaxial irrigation and aspiration tubes 160 and 162 are employed. The irrigation fluid outlet aperture is shown at reference 164.

It will be appreciated by those skilled in the art that the invention is not limited to what has been shown and described hereinabove. Rather, the scope of the invention is limited solely by the claims which follow.

I claim:

1. A method for eye surgery on target tissue in the eye including the steps of coupling a laser to a surgical probe apparatus defining a radiation inlet and a radiation outlet, moving the probe apparatus adjacent to the target tissue in the eye, injecting a precisely controllable volume of air between the radiation outlet and the target tissue, and providing laser radiation from the laser through the probe apparatus to the target tissue while maintaining the volume of air between the probe apparatus and the target tissue, thereby to prevent physical contact between the radiation outlet and the target tissue during laser irradiation.

2. A surgical method according to claim 1 and operative for cataract emulsification and wherein said step of providing laser radiation comprises the steps of irradiating the cataract with a pulse of radiation from a laser, removing the cataract debris created thereby, and repeating the steps of irradiating and removing until the cataract is removed.

3. A method of cataract emulsification according to claim 2 and wherein said step of irradiating the cataract with a pulse of radiation from a laser includes irradiating from a laser selected from the group including a Neodymium YAG, carbon dioxide and Erbium YLF laser.

4. A method according to claim 2 and wherein said step of providing laser radiation comprises the step of irradiating the cataract with a pulse of radiation from an Erbium YLF laser.

* * * * *